United States Patent [19]

Namiki et al.

[11] Patent Number: 4,708,820
[45] Date of Patent: Nov. 24, 1987

[54] METHOD OF PRODUCING PHENOL-TYPE NATURAL ANTIOXIDATIVE MATERIALS FROM PROCESSED SESAME SEED PRODUCTS

[75] Inventors: Mitsuo Namiki; Toshihiko Osawa; Yasuko Fukuda, all of Nagoya; Tatsuhiko Ozaki, Nishio, all of Japan

[73] Assignee: Takemoto Yushi Kabushiki Kaisha, Aichi, Japan

[21] Appl. No.: 802,512

[22] Filed: Nov. 27, 1985

[30] Foreign Application Priority Data

Jun. 26, 1985 [JP] Japan .............................. 60-140056

[51] Int. Cl.$^4$ ...................... C09K 15/34; C09K 15/08
[52] U.S. Cl. ................................... 252/398; 252/404; 426/542; 426/545; 549/435; 549/464
[58] Field of Search ................ 426/542, 545; 549/435, 549/464; 252/398, 404

[56] References Cited

U.S. PATENT DOCUMENTS

| | | | |
|---|---|---|---|
| 2,093,971 | 9/1937 | Musher | 252/398 X |
| 2,095,740 | 10/1937 | Grettie | 252/398 X |
| 2,461,807 | 2/1949 | Buxton et al. | 252/398 X |
| 2,467,903 | 4/1949 | Omohundro et al. | 549/435 |
| 2,467,904 | 4/1959 | Omohundro et al. | 549/435 |
| 2,557,956 | 6/1951 | Feinstein et al. | 549/435 |

FOREIGN PATENT DOCUMENTS

| | | | |
|---|---|---|---|
| 132076 | 8/1983 | Japan | 252/398 |
| 157086 | 9/1984 | Japan | 549/435 |
| 157173 | 9/1984 | Japan | 252/398 |

Primary Examiner—Matthew A. Thexton
Attorney, Agent, or Firm—Flehr, Hohbach, Test, Albritton & Herbert

[57] ABSTRACT

Phenol-type natural antioxidative materials containing analogs of sesamin or sesamolin are manufactured by processing a processed sesame speed product with an acid catalyst and subsequently condensing and separating the desired materials by a physical means such as extraction, distillation and adsorption. By qualitative analysis, the phenol-type natural antioxidative material thus concentrated and separated by a method of the present invention is found to contain analogs of sesamin (A, B and C) and sesamolin (D) having the following chemical structures:

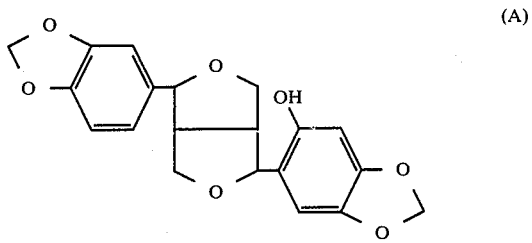

(A)

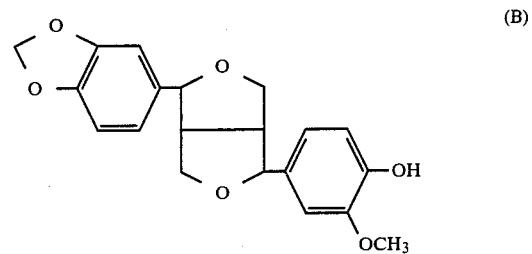

(B)

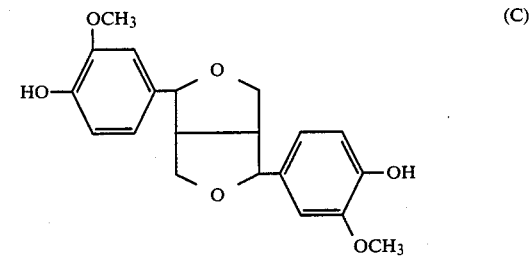

(C)

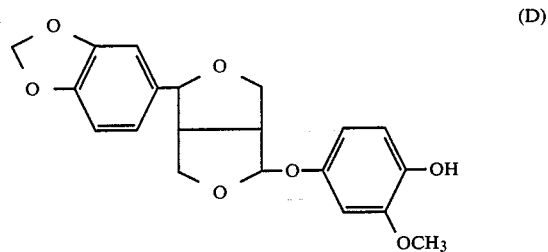

(D)

4 Claims, No Drawings

METHOD OF PRODUCING PHENOL-TYPE NATURAL ANTIOXIDATIVE MATERIALS FROM PROCESSED SESAME SEED PRODUCTS

This invention relates to a method of manufacturing phenol-type natural antioxidative materials containing analogs of sesamin or sesamolin from processed sesame seed products.

Sesame seed oil is known to contain not only sesamolin and sesamin which are natural antioxidative materials peculiar to sesame seeds but also tocopherols which are widely found also in other vegetable oils, and that these natural antioxidative materials are significantly contributing to the stability of sesame seed oil against oxidation. Regarding other natural antioxidative materials contributing to the stability of sesame seed oil against oxidation, however, there are still many properties remaining unknown and there has hardly been any attempt to extract such materials in an industrially advantageous manner. The present invention thus relates to a method of manufacturing such natural antioxidative materials in an industrially advantageous manner.

The present inventors have earlier disclosed that various aglycons with antioxidative properties can be obtained by enzymatic hydrolysis of glycosides obtainable by extraction from processed sesame seed products by using β-glucosidase (Japanese Patent Tokkai No. 59-157173). Among the aglycons obtained are analogs of sesamin or sesamolin such as tetrahydro-1-[6-hydroxy-3,4-(methylene dioxy) phenyl]-4-[3,4-(methylene dioxy)phenyl]-1H,3H-furo[3,4-C] furan (a compound shown later by letter A), tetrahydro-1-[3-methoxy-4-hydroxy phenyl]-4-[3,4-(methylene dioxy) phenyl]-1H,3H-furo [3,4-C] furan (a compound shown later by B), tetrahydro-1-[3-methoxy-4-hydroxy phenoxy]-4-[3,4-(methylene dioxy)phenyl]-1H,3H-furo [3,4-C] furan (a compound shown later by D), etc.

Since the aforementioned aglycons exist within processed sesame seed products as glycosides combined with various types of saccharides, the yield of aglycons is low by the aforementioned conventional method which, requiring complicated operations, was not appropriate for industrial applications.

It is therefore an object of this invention to provide a new method of manufacturing phenol-type natural antioxidative materials which eliminates the aforementioned problems of the conventional methods.

In view of the situation described above, the present inventors diligently investigated an industrially feasible means for directly obtaining from sesame seeds natural antioxidative materials containing analogs of sesamin or sesamolin and made an unexpected discovery that the concentration of such analogs of sesamin or sesamolin increases not only several times but several tens of times and moreover a large amount of the compound shown by A which is hardly contained in the original sesame seed product is produced if processed products of sesame seeds are treated with a catalyst. A new method of manufacturing phenol-type natural antioxidative materials containing analogs of sesamin or sesamolin has thus been established. Stated briefly, this invention teaches a method of manufacturing phenol-type natural antioxidative materials containing analogs of sesamin or sesamolin characterized in that after a processed product of sesame seeds are subjected to an acid catalyst processing, physical processing means such as extraction, distillation and/or adsorption are used for concentration and separation.

The processed sesame seed products which may be used according to the present invention include the following sesame oils and paste-like substances: unrefined sesame seed oils extracted mechanically, for example, by pressing from raw or roasted sesame seeds, unrefined sesame seed oils extracted from such seeds by using an organic solvent such as hexane, refined sesame seed oils obtained from these unrefined sesame seed oils by chemical or physical processing such as removing of free acid, bleachings and filtering, and paste-like materials obtained by crushing or milling seeds of the aforementioned types.

The acid catalysts which may be used according to this invention include the following Bronsted acids, Lewis acids and solid catalysts having the functions of an acid catalyst: various inorganic and organic Bronsted acids such as hydrochloric acid, sulfuric acid, phosphoric acid, boric acid and p-toluenesulfonic acid, Lewis acids such as aluminum chloride, titanium chloride, tin chloride and boron trifluoride, and solid catalysts having the functions of an acid catalyst such as acid clay, activated clay, zeolite, silica-titanium oxide and cation exchange resins. The above may be used singly or two or more may be used in combination. For the convenience of operation, however, it is preferable to use a solid catalyst with the functions of an acid catalyst. The acid catalyst processing may be carried out either by adding an acid catalyst to a processed sesame seed product and, if necessary, heating and stirring the mixture (from room temperature to about 210° C.) or by heating and stirring in a solvent system of a solution or dispersion system (temperature up to the boiling point of the solvent).

Many mehods are available to the present invention for carrying out the process of concentration and separation of phenol-type natural antioxidative materials after the acid catalyst processing step. They include the following physical methods of extraction, distillation and/or adsorption which can be used together in appropriate combinations.

For extraction, there is the method of adding a polar organic solvent (such as methanol) with small solubility regarding sesame seed oil (triglyceride of fatty acid) to extract the desired material after the step of processing with an acid catalyst and distilling or evaporating the polar organic solvent from this extract solution for concentration and separation. Another method is to add an alkali water solution such as alkali hydroxide or alkali carbonate (or a mixture of alkali water solution and water-soluble solvent) to the product processed with an acid catalyst for extraction by stirring or shaking. After it is separated into an oil layer and a water layer or a layer of the aforementioned mixture (only the case of water layer to be considered hereinafter), a mineral or organic acid is added to this water layer to neutralize it. After an additional amount of acid is introduced to make it an acidic system, an organic solvent not soluble in water such as ethyl acetate, diethyl ether and xylene is used to extract the desired material and the solvent is finally distilled or evaporated away to complete the concentration and separation.

As for distillation, there is the method of obtaining a crude distillate by introducing steam of 100°–200° C. under a normal or reduced pressure into a system processed with an acid catalyst and concentrating and separating the desired material by removing free fatty acid and glycerides from this crude distillate by the aforementioned extraction method. There is also the method by molecular distillation of the processed material from the acid catalyst step.

As for adsorption, there is the method of separating by filtering or centrifugal separation the solid catalyst component to which the desired material is adsorbed and then by using the aforementioned extraction method to concentrate and separate the desired material. Another method is to use an adsorbent such as silica gel, silica/alumina, alumina, anion exchange resin, activated charcoal, etc. either in the presence or absence of an organic solvent to carry out an adsorption process (to be repeated several times, if necessary) on the product after the aforementioned processing with an acid catalyst and then to concentrate and separate the desired material from this adsorbent by the aforementioned extraction method. Still another method is to use an adsorbent at the same time as when a solid catalyst is used for the acid catalyst processing and to concentrate and separate the desired material from this adsorbent by the aforementioned extraction method.

Details will be presented below with examples but, of the methods of extraction, distillation and/or adsorption described above, it is preferable to use one or more of the following methods of concentration and separation on the product after the acid catalyst processing so that highly concentrated phenol-type natural antioxidative materials can be obtained: the method of separating triglyceride by cooling and precipitating in the presence of a polar organic solvent ((r) of Example 6 below), the method of simultaneously or separately extracting by using a non-polar organic solvent (such as hydrocarbon-type organic solvents) and an aqueous organic solvent (such as a mixture of water and lower alcohol and preferably alkeline) ((o) of Example 3, (p) of Example 4, (q) of Example 5 and (s) of Example 7 below), and the method of molecular distillation ((s) of Example 7 below).

By identification, the phenol-type natural antioxidative material thus concentrated and separated by a method of the present invention is found to contain analogs of sesamin (A, B and C) and sesamolin (D) having the following chemical structures:

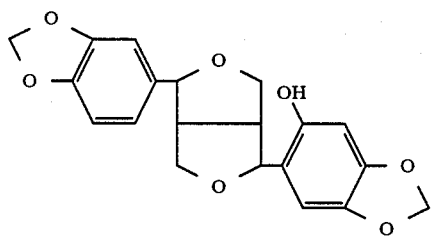
(A)

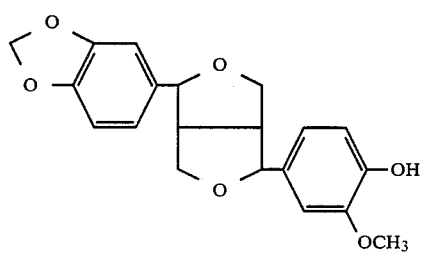
(B)

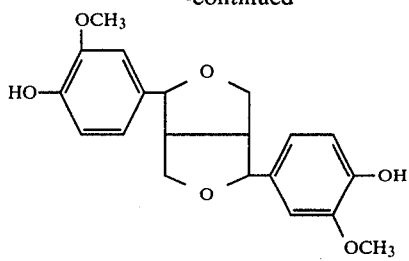
(C)

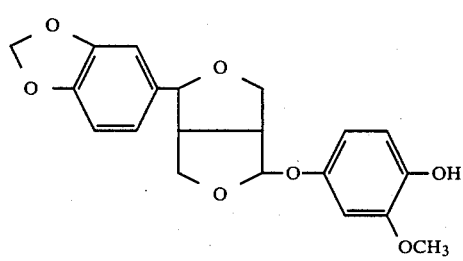
(D)

Of the above A, B and D have been named above. The compound C is tetrahydro-1,4-bis[3-methoxy-4-hydroxyphenyl]-1H,3H-furo[3,4-C] furan (pinoresinol).

In what follows, the present invention and its effects will be explained by way of examples.

(1) Effects of Processing With Acid Catalysts on Processed Sesame Seeds

Acetone-extracted raw sesame seed oil (S-1) was prepared by pressing raw sesame seeds and distilling the acetone extract at a reduced pressure and at a temperature below 40° C. to remove acetone. Separately, pressed raw sesame seed oil (S-2) was prepared by pressing the same raw sesame seeds to extract oil and filtering it. Further separately, pressed raw sesame seed oil processed with acid catalyst (S-3) was prepared by adding one weight percent of activated clay to the pressed raw sesame seed oil (S-2) and filtering it after stirring the mixture for one hour at 70° C. Table 1 shows the results of analysis on S-1, S-2 and S-3.

TABLE 1

|     | A    | B   | C   | D    | E    | F  |
|-----|------|-----|-----|------|------|----|
| S-1 | ND   | 3.7 | 4.1 | 1.5  | ND   | ND |
| S-2 | ND   | 1.3 | 3.6 | 1.1  | 47.9 | T  |
| S-3 | 81.9 | 8.1 | 9.0 | 11.2 | 25.5 | T  |

In Table 1, the numbers are in units of $10^{-3}$ wt %. A-D are the compounds described before. E and F represent γ-tocopherol and sesamol, respectively. ND and T signify "not detected" and "traces only", respectively. The analyses were carried out as follows by high-speed liquid chromatography (column: Dvelosil, ODS-10, 8 mmφ×250 mm). For A, B, C and D, the solvent was methanol/water=6/4, the flow rate was 5 ml/min and the retention time was 11.8 min, 6.4 min, 2.7 min and 8.6 min respectively for A, B, C and D. For E, the solvent was methanol, the flow rate was 5 ml/min and the retention time was 8.5 min. For F, the solvent was methanol/water=3/7, the flow rate was 4 ml/min, and the retention time was 10.4 min.

(2) Example 1

An expeller was used to extract oil from raw sesame seeds from China and pressed raw sesame seed oil (a) was obtained by filtering. Next, coexisting free fatty acids were removed from it by washing it with a caustic soda solution and also with water. Refined sesame seed oil (b) thus obtained (100 kg) was dehydrated under a reduced pressure at 70° C. and 1 kg of acid clay was added as acid catalyst. After 30 minutes of processing at 70° C., the mixture was filtered to obtain 98 kg of acid catalyst processed oil (c) and 2 kg of acid clay filtered residue (d).

Steam at 150°-160° C. was introduced into (c) for distillation under a reduced pressure and steam distilled sesame seed oil (e) and 0.95 kg of steam distilled residue (f) were obtained. Separately, 100 g of (d) was taken inside a triangular flask of capacity 500 ml, 300 ml, of ethyl acetate was added and the mixture was heated at 60° C. for 30 minutes on a bath with an air condenser. After it was cooled down to room temperature, acid clay residue was filtered away and ethyl acetate was distilled away under a reduced pressure to obtain 39 g of ethyl acetate extract (g). By similar processes, 17.5 g of n-hexane extract (h), 22.0 g of acetone extract (i) and 5.1 g of ethanol extract (j) were also obtained from (d). Table 2 shows the results of analysis on (g), (h), (i) and (j). Letters A-F are as explained in connection with Table 1.

(3) Example 2

Into a triangular flask of capacity 500 ml, 100 g of (f) of Example 1 was taken and 300 ml of ethyl acetate was added. The mixture was heated at 60° C. for 30 minutes on a bath with an air condenser. After it was left overnight at 10° C., it was filtered and the solvent was removed to obtain 80 g of ethyl acetate extract (k). By similar processes, 49 g of methanol extract (l) and 61 g of ethanol extract (m) were obtained. Table 2 also shows the results of analysis on (k), (l) and (m).

(4) Example 3

In 200 ml of n-hexane was dissolved 100 g of (e) of Example 1, and after 200 ml of methanol was added and the mixture was shaken, it was left quietly to separate a methanol layer. Solvent was removed from this methanol layer to obtain 3.0 g of extract (n). Separately therefrom, 100 g of (e) Example 1 was dissolved in 200 ml of n-hexane, and after 140 ml of ethanol and 60 ml of water were added and the mixture was shaken, it was left quietly to separate the ethanol/water layer. Solvent was removed from this ethanol/water layer to obtain 0.32 g of extract (o). Table 2 also shows the results of analysis of (n) and (o).

(5) Example 4

In 200 ml of n-hexane was dissolved 100 g of (e) of Example 1, and after 140 ml of ethanol and 60 ml of 0.3N water solution of caustic soda were added and the mixture was shaken, it was left quietly to separate a ethanol/water layer. Hydrochloric acid was added to adjust the pH value of this ethanol/water layer to 2 and after 200 ml of ethyl ether was added and the mixture was shaken, the separated ethyl ether layer was washed until the washing water became neutral. After anhydrous sodium sulfate was used for dehydration, it was filtered and solvent was removed to obtain 0.77 g of extract (p). Table 2 shows the results of analysis on (p).

(6) Example 5

The same raw sesame seeds used in Example 1 were roasted first and oil was extracted and filtered. Into 100 g of roasted sesame seed oil thus obtained was added 1 g of aluminum chloride and the mixture was heated and stirred for 30 minutes at 70° C. After it was cooled to room temperature, 200 ml of hexane, 100 ml of 0.5N water solution of caustic soda and 100 ml of ethanol were added, and the mixture was stirred well to separate an ethanol/water layer. Hydrochloric acid was added to adjust the pH value of this ethanol/water layer to 2 and after 100 ml of xylene was added and the mixture was shaken, the xylene layer obtained by leaving the mixture quietly was washed with water until the washing water became neutral. After anhydrous sodium sulfate was used for dehydration, it was filtered and solvent was removed to obtain 2.2 g of extract (q). Table 2 shows the results of analysis on (q).

(7) Example 6

Into the paste-like material obtained by crushing in a mill 1 kg of the same raw sesame seeds used in example 1, 3 l of methanol was added and the mixture was stirred well. The extract solution thus obtained by filtering was left overnight at $-20°$ C. to cause triglyceride to be deposited. After this was filtered, 10 g of 35% hydrochloric acid was added. After 30 minutes in a reflux, it was cooled to room temperature, 2 l of xylene and 2 l of water were added and the mixture was shaken to separate a xylene layer. This xylene layer was washed with water until the washing water became neutral and solvent was removed to obtain 8.1 g of extract (r). Table 2 shows the results of analysis on (r).

(8) Example 7

Under the condition of 210° C.×4 mmHg, 100 kg of the acid catalyst processed oil (c) obtained by the method described in Example 1 was subjected to molecular distillation to obtain 0.8 kg of distillate. This distillate was dissolved in 4 l of xylene, and after 1 l of 0.5N water solution of caustic soda and 3 l of isopropyl alcohol were added and the mixture was well shaken, it was left quietly and an isopropyl alcohol/water layer was obtained by separation. Hydrochloric acid was added to adjust its pH value to 2 and 2 l of xylene was used for extraction. After the xylene layer was washed with water until the washing water became neutral, solvent was removed to obtain 220 g of xylene extract. This xylene extract was dispersed in 1 l of hexane and after 30 minutes in a reflux, it was left quietly and substances soluble in hexane were filtered to obtain 21 g of extract (s) not soluble in hexane. Table 2 also shows the results of analysis on (s).

TABLE 2

|     | A     | B    | C     | D     | E    | F    |
| --- | ----- | ---- | ----- | ----- | ---- | ---- |
| (g) | 0.77  | 0.07 | 0.07  | 0.12  | 0.06 | T    |
| (h) | 0.06  | 0.01 | T     | 0.02  | 0.05 | T    |
| (i) | 0.68  | 0.07 | 0.09  | 0.12  | 0.05 | T    |
| (j) | 1.13  | 0.15 | 0.27  | 0.34  | 0.05 | 0.01 |
| (k) | 0.82  | 0.04 | 0.05  | 0.11  | 0.52 | 0.02 |
| (l) | 1.02  | 0.05 | 0.07  | 0.18  | 0.50 | 0.03 |
| (m) | 0.91  | 0.05 | 0.07  | 0.18  | 0.61 | 0.02 |
| (n) | 1.85  | 0.19 | 0.20  | 0.31  | 0.04 | ND   |
| (o) | 8.57  | 0.84 | 0.92  | 0.65  | T    | 0.01 |
| (p) | 12.15 | 0.89 | 1.25  | 1.33  | ND   | T    |
| (q) | 10.10 | 0.72 | 1.29  | 1.00  | ND   | 0.28 |
| (r) | 7.14  | 0.82 | 0.99  | 1.42  | T    | T    |
| (s) | 52.70 | 8.60 | 10.10 | 10.30 | T    | 0.20 |

(9) Tests of Antioxidative Characteristics

As examples of phenol-type natural antioxidative materials, 100 mg of (g), 40 mg of (o), 40 mg of (q) and 4 mg of (s) were individually taken into a triangular flask of capacity 100 ml. Likewise, 4 mg of dl-α-tocopherol and 40 mg of commercially available natural antioxidant (SP-10 by Lion McCormick Company) were separately taken into a flask and 20 g of bean oil refined through a base alumina column was added to each of these flasks which were subsequently shaken well. They were kept inside an oven at 98° C. and the amount of peroxide (meq/kg) was measured according to a usual procedure over a period of time. The results are shown in Table 3.

TABLE 3

|  | 0 hr | 3 hr | 5 hr | 7 hr | 10 hr | 15 hr |
|---|---|---|---|---|---|---|
| (g) | 3.7 | 11 | 17 | 26 | 55 | 156 |
| (o) | 3.7 | 10 | 17 | 23 | 37 | 80 |
| (q) | 3.7 | 10 | 16 | 23 | 34 | 57 |
| (s) | 3 7 | 12 | 18 | 26 | 42 | 69 |
| dl-α-tocopherol | 3.7 | 12 | 18 | 25 | 38 | 101 |
| commercial natural antioxidant | 3.7 | 11 | 28 | 54 | 112 | 200< |
| no addition | 3.7 | 62 | 102 | 143 | 200< | — |

The examples and experimental results (Tables 1–3) shown above make it clear that the present invention provides an industrially applicable method including acid catalyst processing and subsequent concentration-separation steps to manufacture phenol-type natural antioxidative materials containing a large amount of substances having analogous structures to sesamin or sesamolin which exhibit excellent antioxidative characteristics and in particular the compound shown by A which is produced in a large quantity.

What is claimed is:

1. A method of manufacturing phenol-type natural antioxidative materials containing analogs of sesamin or sesamolin comprising the steps of processing a processed sesame seed product with an acid catalyst, and subsequently concentrating and separating said materials by a physical means such as extraction, distillation and adsorption, said acid catalyst being one or more selected from the group which consists of Brønsted acids, Lewis acids, acid clay, activated clay, zeolite, silica-titanium oxide and cation exchange resins.

2. The method of claim 1 wherein said analog of sesamin contains one or more of the compounds shown by A, B and C:

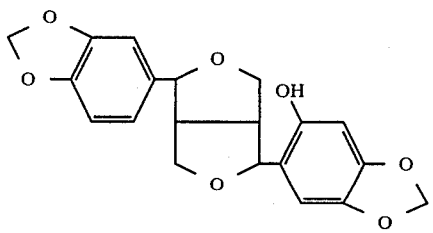

(A)

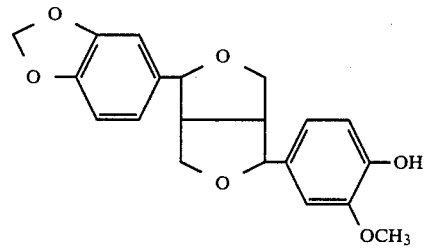

(B)

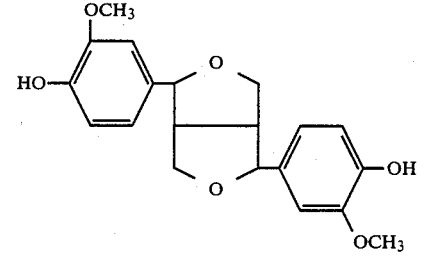

(C)

3. The method of claim 1 wherein said analog of sesamolin is a compound shown by the chemical formula D below:

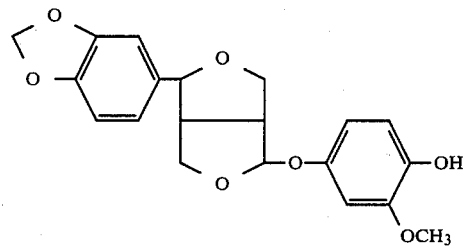

(D)

4. The method of claim 2 wherein said analog of sesamin contains as its principal component a compound shown by the chemical formula A.

* * * * *

UNITED STATES PATENT AND TRADEMARK OFFICE
CERTIFICATE OF CORRECTION

PATENT NO. : 4,708,820
DATED : November 24, 1987
INVENTOR(S) : MITSUO NAMIKI, et al.

It is certified that error appears in the above-identified patent and that said Letters Patent are hereby corrected as shown below:

Column 3, line 36, after "aqueous" and before "organic"

insert ---polar---.

Signed and Sealed this

Twenty-sixth Day of April, 1988

Attest:

DONALD J. QUIGG

Attesting Officer
Commissioner of Patents and Trademarks